US009585978B2

(12) United States Patent
Ogawa

(10) Patent No.: US 9,585,978 B2
(45) Date of Patent: Mar. 7, 2017

(54) ELECTRON BEAM STERILIZATION DEVICE AND STERILE FILLING EQUIPMENT

(71) Applicant: HITACHI ZOSEN CORPORATION, Osaka-shi, Osaka (JP)

(72) Inventor: Satoshi Ogawa, Osaka (JP)

(73) Assignee: HITACHI ZOSEN CORPORATION, Osaka-shi, Osaka (JP)

( * ) Notice: Subject to any disclaimer, the term of this patent is extended or adjusted under 35 U.S.C. 154(b) by 0 days.

(21) Appl. No.: 14/909,537

(22) PCT Filed: May 22, 2014

(86) PCT No.: PCT/JP2014/063529
§ 371 (c)(1),
(2) Date: Feb. 2, 2016

(87) PCT Pub. No.: WO2015/019676
PCT Pub. Date: Feb. 12, 2015

(65) Prior Publication Data
US 2016/0175466 A1  Jun. 23, 2016

(30) Foreign Application Priority Data

Aug. 5, 2013  (JP) .................................. 2013-161973

(51) Int. Cl.
*A61L 2/08* (2006.01)
*G21K 5/10* (2006.01)
(Continued)

(52) U.S. Cl.
CPC ................ *A61L 2/087* (2013.01); *G21K 5/10* (2013.01); *A61L 2202/23* (2013.01);
(Continued)

(58) Field of Classification Search
CPC ........ A61L 2/08; A61L 2/087; A61L 2202/23; G21K 5/00; G21K 5/02; G21K 5/04;
(Continued)

(56) References Cited

U.S. PATENT DOCUMENTS 7,579,607 B2 *  8/2009  Dumargue ................ A23L 3/26
                                              250/453.11
2011/0012030 A1 *  1/2011  Bufano .................... A61L 2/087
                                              250/492.3
(Continued)

FOREIGN PATENT DOCUMENTS

EP         2394950 A1    12/2011   ............... B67C 7/00
JP         2007-106438    4/2007   ............. B65B 55/24
(Continued)

OTHER PUBLICATIONS

International Search Report issued in corresponding International Patent Application No. PCT/JP2014/063529, dated Aug. 26, 2014.

*Primary Examiner* — David E Smith
(74) *Attorney, Agent, or Firm* — Kusner & Jaffe

(57) ABSTRACT

A circular sterilization path (CD) is divided into a front sterilization path (Pd) having a preform sterilization section formed and a rear sterilization path (Bd) having a molded-container sterilization section formed. A single electron beam sterilization device simultaneously sterilizes a preform (P) and a molded container (B), achieving effective sterilization and a size reduction of equipment.

5 Claims, 6 Drawing Sheets

(51) Int. Cl.
    *B29C 49/36*     (2006.01)
    *B67C 3/22*     (2006.01)
    *B29C 49/06*     (2006.01)
    *B29C 49/46*     (2006.01)

(52) U.S. Cl.
    CPC .............. *B29C 49/06* (2013.01); *B29C 49/36* (2013.01); *B29C 2049/4682* (2013.01); *B29C 2049/4697* (2013.01); *B67C 2003/227* (2013.01)

(58) Field of Classification Search
    CPC .......... G21K 5/10; B29C 49/06; B29C 49/36; B29C 49/2049; B29C 49/4682; B29C 49/4697
    See application file for complete search history.

(56) References Cited

U.S. PATENT DOCUMENTS

| | | | |
|---|---|---|---|
| 2011/0061343 A1* | 3/2011 | Roithmeier | B29C 49/42 53/452 |
| 2013/0154164 A1* | 6/2013 | Laumer | B29C 49/4205 264/535 |
| 2014/0299786 A1 | 10/2014 | Yokobayashi et al. | 250/455.11 |

FOREIGN PATENT DOCUMENTS

| | | | | |
|---|---|---|---|---|
| JP | 2010-202284 | 9/2010 | ............. | B65B 55/10 |
| JP | 2011-56943 | 3/2011 | ............. | B29C 49/08 |
| JP | 2013-86822 | 5/2013 | ............. | B65B 55/08 |

* cited by examiner

ELECTRON BEAM STERILIZATION DEVICE AND STERILE FILLING EQUIPMENT

RELATED APPLICATIONS

This application is a National Stage of International Application No. PCT/JP2014/063529, filed May 22, 2014, which claims the benefit of Japanese Patent Application No. 2013-161973, filed Aug. 5, 2013.

FIELD OF THE INVENTION

The present invention relates to an electron beam sterilization device that sterilizes both a preform (parison or preformed article) and a molded article during sterilization of a container formed by blow molding, and sterile filling equipment.

BACKGROUND OF THE INVENTION

Japanese Patent Laid-Open No. 2011-56943 discloses a device that performs preliminary sterilization on a preform before blow molding with a gaseous medium containing heat-treated oxygenated water or electron beams, performs main sterilization on a molded container, which is formed by blow molding, with the gaseous medium or electron beams, and then fills the molded container.

The device can effectively sterilize a durable preform, only requiring slight main sterilization for a short time.

The invention described in Patent Literature 1, however, requires the installation of sterilization devices at the entrance and exit of a blow molding machine, disadvantageously increasing the overall size of equipment.

The present invention has been devised to solve the problem. An advantage of the present invention is an electron beam sterilization device that can reduce the overall size of equipment and satisfactorily sterilize a container, and sterile filling equipment.

SUMMARY OF THE INVENTION

An electron beam sterilization device according to a first aspect is an electron beam sterilization device capable of simultaneously sterilizing a molded container and a preform of the molded container,
the electron beam sterilization device including:
electron beam irradiation nozzles that are protruded at regular intervals and are moved along an endless sterilization path;
container holders that are moved along the sterilization path so as to hold the molded container and the preform; and
a nozzle inserting/removing device that moves one of the container holder and the electron beam irradiation nozzle to the other so as to insert and remove the electron beam irradiation nozzle into and from the molded container and the preform,
wherein the sterilization path partially serves as a front sterilization path where a container carrier device holds and transports the preform while the other part of the transport path serves as a rear sterilization path where the container carrier device holds and transports the molded container,
the front sterilization path has a preform sterilization section where the nozzle inserting/removing device inserts the distal end of the electron beam irradiation nozzle into the preform from an opening portion and internally sterilizes the preform while the rear sterilization path has a molded-container sterilization section where the nozzle inserting/removing device inserts the distal end of the electron beam irradiation nozzle into the molded container from the opening portion and internally sterilizes the molded container.

An electron beam sterilization device according to a second aspect, in the configuration of the first aspect, further includes a front external electron-beam emitter on a preform entrance path connected to the entrance of the front sterilization path, the front external electron-beam emitter sterilizing the outer surface of the preform with electron beams; and
a rear external electron-beam emitter on a molded-container entrance path connected to the entrance of the rear sterilization path, the rear external electron-beam emitter sterilizing the outer surface of the molded container.

An electron beam sterilization device according to a third aspect, wherein the preform and the molded container have neck portions that are substantially identical in shape, and the container holder includes a pair of clamp arms capable of holding the neck portions of the preform and the molded container.

Sterile filling equipment according to a fourth aspect is sterile filling equipment including a blow molding device that forms a molded container by performing blow molding on the preform of the molded container, and a filling device that fills, with a filling fluid, the molded container formed by the blow molding device,
the sterile filling equipment further including the electron beam sterilization device according to one of the first to third aspects, the electron beam sterilization device sterilizing the preform before transportation into the blow molding device and the molded container ejected from the blow molding device.

Sterile filling equipment according to a fifth aspect, in the configuration of the fourth aspect, further includes a preform preheating device on a transport path from the preform sterilization section to the blow molding device; and
a molded-container cleaning device on a transport path from the molded-container sterilization section to the filling device.

Advantageous Effects of Invention

According to the electron beam sterilization device of the first aspect, the single endless sterilization path is divided into the front sterilization path and the rear sterilization path, the preform sterilization section for sterilizing the preform is provided on the front sterilization path, and the molded-container sterilization section for sterilizing the molded container is provided on the rear sterilization path. Therefore, the preform and the molded container can be simultaneously sterilized by the single electron beam sterilization device, achieving more reliable sterilization.

According to the electron beam sterilization device of the second aspect, the preform and the molded container are internally sterilized in a sequential manner after external sterilization. This can prevent contaminants on an sterilized portion from contaminating the unsterilized portion.

According to the electron beam sterilization device of the third aspect, the preform and the molded container having the neck portions identical in shape are used, and thus the clamp arms identical in shape for moving the preform or the molded container on the sterilization path can be used and the clamp arms can hold the neck portions according to the same operation. This can simplify the sterilization device with a small size.

According to the sterile filling equipment of the fourth aspect, when the molded container formed by the blow molding device undergoes aseptic filling, the preform sterilized with electron beams is subjected to blow molding into the molded container, and then the molded container is further sterilized with electron beams. Thus, effective sterilization and aseptic filling can be performed on the molded container. Moreover, this can reduce the sterilization time and intensity of electron beams of the molded container. Furthermore, the preform and the molded container are sterilized by the integrated electron beam sterilization device, thereby reducing the size of the equipment.

BRIEF DESCRIPTION OF DRAWINGS

FIG. 7A is a schematic longitudinal section of a first modification, and FIG. 7B is a schematic longitudinal section of a second modification.

DETAILED DESCRIPTION OF THE PREFERRED EMBODIMENTS

First Embodiment

Referring to FIGS. 1 to 6, an embodiment of sterile filling equipment according to the present invention will be described below.

Figure 6A:
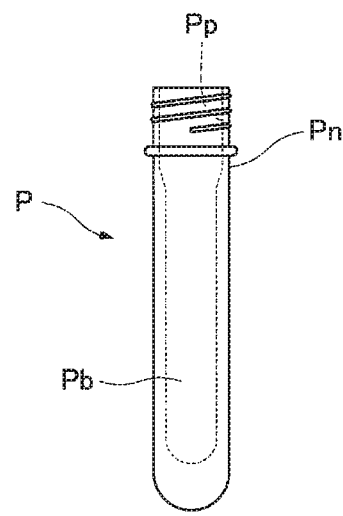
FIG. 6A is a side view of a preform and FIG. 6B is a side view of a molded container.
Figure 6B:
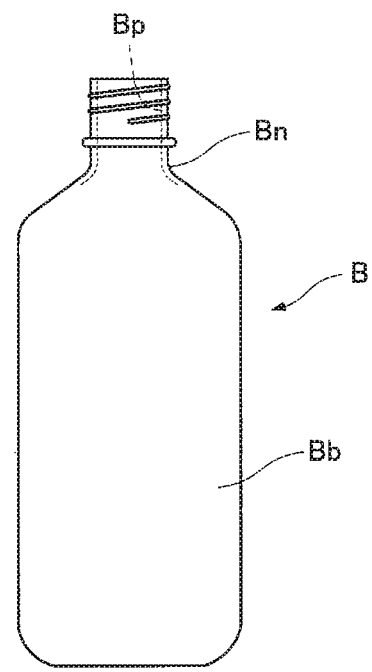

The sterile filling equipment preheats a preform P (parison or preformed article), which has been injection-molded according to a cold parison technique as shown in FIG. 6A, to a drawing temperature, forms a molded container B by blow molding as shown in FIG. 6B, and then fills the molded container B. In the sterile filling equipment, the preform P before blow molding and the molded container B after blow molding are subjected to sterilization and sterile filling by a single electron beam sterilization device, achieving effective sterilization and a size reduction of the equipment.

Preform

As shown in FIG. 6, the preform P has a neck portion Pn and an opening portion Pp that are precisely formed by injection molding, and a body portion Pb that is U-shaped in longitudinal section. The molded container B includes a neck portion Bn and an opening portion Bp that are not molded by a blow molding device, and only a body portion Bb molded by the blow molding device. Thus, the preform P and the molded container B have the neck portions Pn and Bn identical in shape and the opening portions Pp and Bp identical in shape.

Outline of the Sterile Filling Equipment

Figure 1:
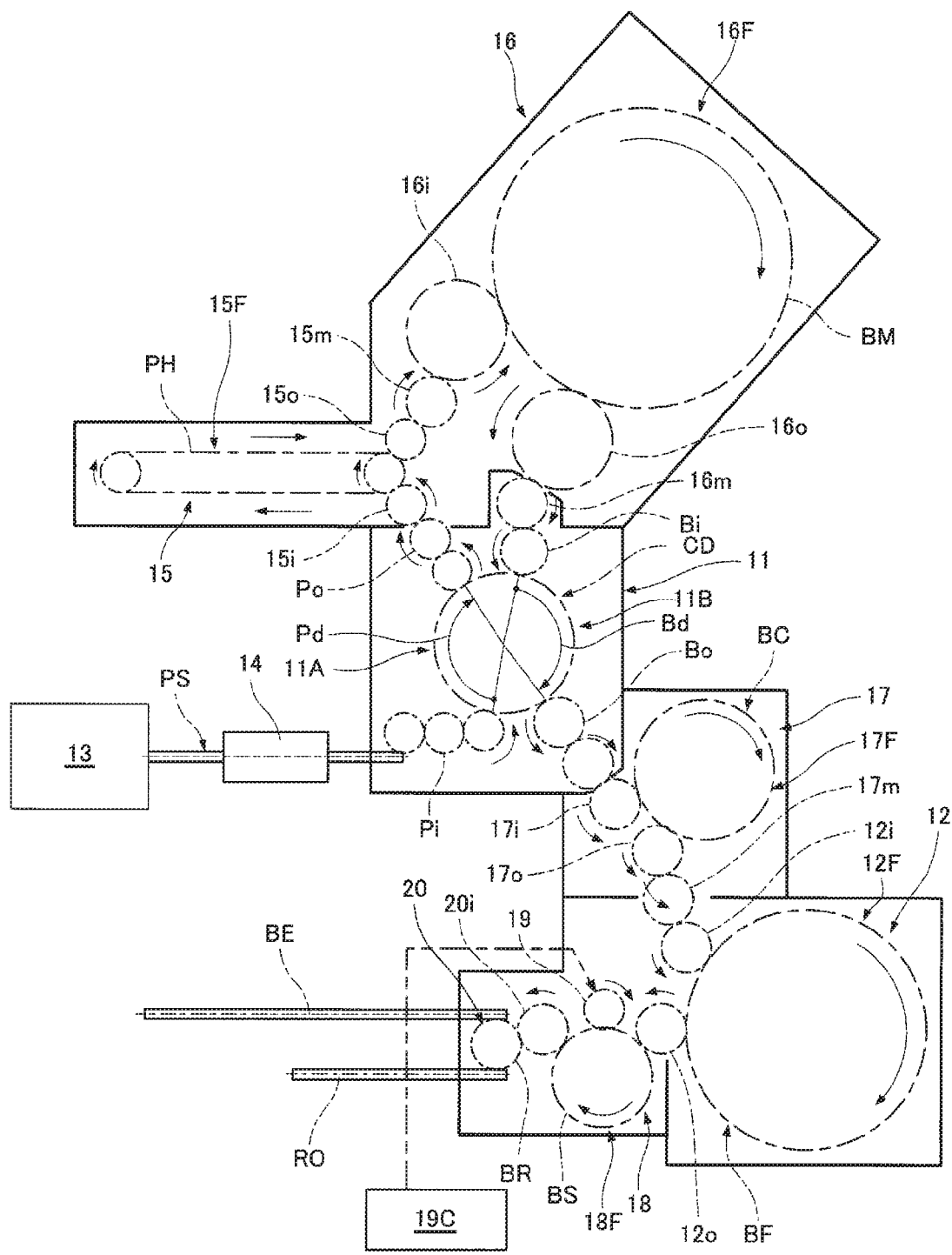
FIG. 1 is a schematic plan view showing a first embodiment of sterile filling equipment according to the present invention.

As shown in FIG. 1, the preform P of the injection-molded container B is supplied from a preform feeder 13 to the entrance of an electron beam sterilization device 11 along a preform supply path PS. The preform supply path PS has a cleaning/positioning device 14 that cleans and positions the preforms P so as to sequentially supply the preforms P to the electron beam sterilization device 11.

The electron beam sterilization device 11 has a sterilization path CD circular in plan view as an example of an endless sterilization path. The sterilization path may be an oblong or oval endless path or a linear or curved reciprocated endless path. The sterilization path CD is divided into a front sterilization path Pd that has a preform sterilization section 11A for sterilizing the inner surface of the preform P and a rear sterilization path Bd that has a molded-container sterilization section 11B for sterilizing the inner surface of the molded container B. The preform P is sterilized on a preform entrance path Pi, which is connected to the entrance of the front sterilization path Pd, and the front sterilization path Pd. The molded container B is sterilized on a molded container entrance path Bi, which is connected to the entrance of the rear sterilization path Bd, and the rear sterilization path Bd.

The sterilized preform P is ejected from a preform exit path Po of the electron beam sterilization device 11, is introduced to an oblong preheating path PH of a preheating device 15 through an exit neck handling wheel 15$i$ so as to be preheated to a molding temperature, and then is supplied to a blow molding device 16 through an exit neck handling wheel 15$o$ for transportation and an entrance neck handling wheel 16$i$. In the blow molding device 16, the preforms P held in molds are transported along a circular molding path BM and are subjected to blow molding, sequentially molding the molded containers B.

The molded container B ejected from the blow molding device 16 through an exit neck handling wheel 16$o$ for transportation is introduced to the molded container entrance path Bi of the electron beam sterilization device 11 so as to be externally sterilized, and then the inner surface of the molded container B is sterilized on the rear sterilization path Bd. Subsequently, the sterilized molded container B is transported into an air rinser (cleaning device) 17 from a container exit path Bo through an entrance neck handling wheel 17$i$.

The air rinser 17 cleans the molded container B by removing fine residues in the sterilized molded container B and ozone captured through the molded-container sterilization section 11B.

Subsequently, the molded container B ejected from the air rinser 17 through an exit neck handling wheel 17$o$ is transported into a filling device 12 through an intermediate neck handling wheel 17$m$ for transportation and an entrance neck handling wheel 12$i$. The molded containers B transported along a circular filling path BF are sequentially filled with a filling liquid. The molded container B from the filling device 12 is transported into a capper 18 through an exit neck handling wheel 12$o$ and is transported on a circular capping path BS by a capping carrier device 18F such that the opening portion Bp of the molded container B is sealed with a cap. Reference numeral 19 denotes a cap supply wheel that supplies caps from a cap cleaning device 19C to the capper 18. The exit of the capper 18 is connected to a rejecting device 20 via an entrance neck handling wheel 20$i$. During transportation on a circular reject path BR, the molded containers B having been normally sterilized and filled are separated from defective containers having been insufficiently sterilized or filled. The normal molded containers B are transported to a container ejection path BE, whereas the defective molded containers B are transported to a reject ejection path RO.

Container Carrier Device

Figure 2:
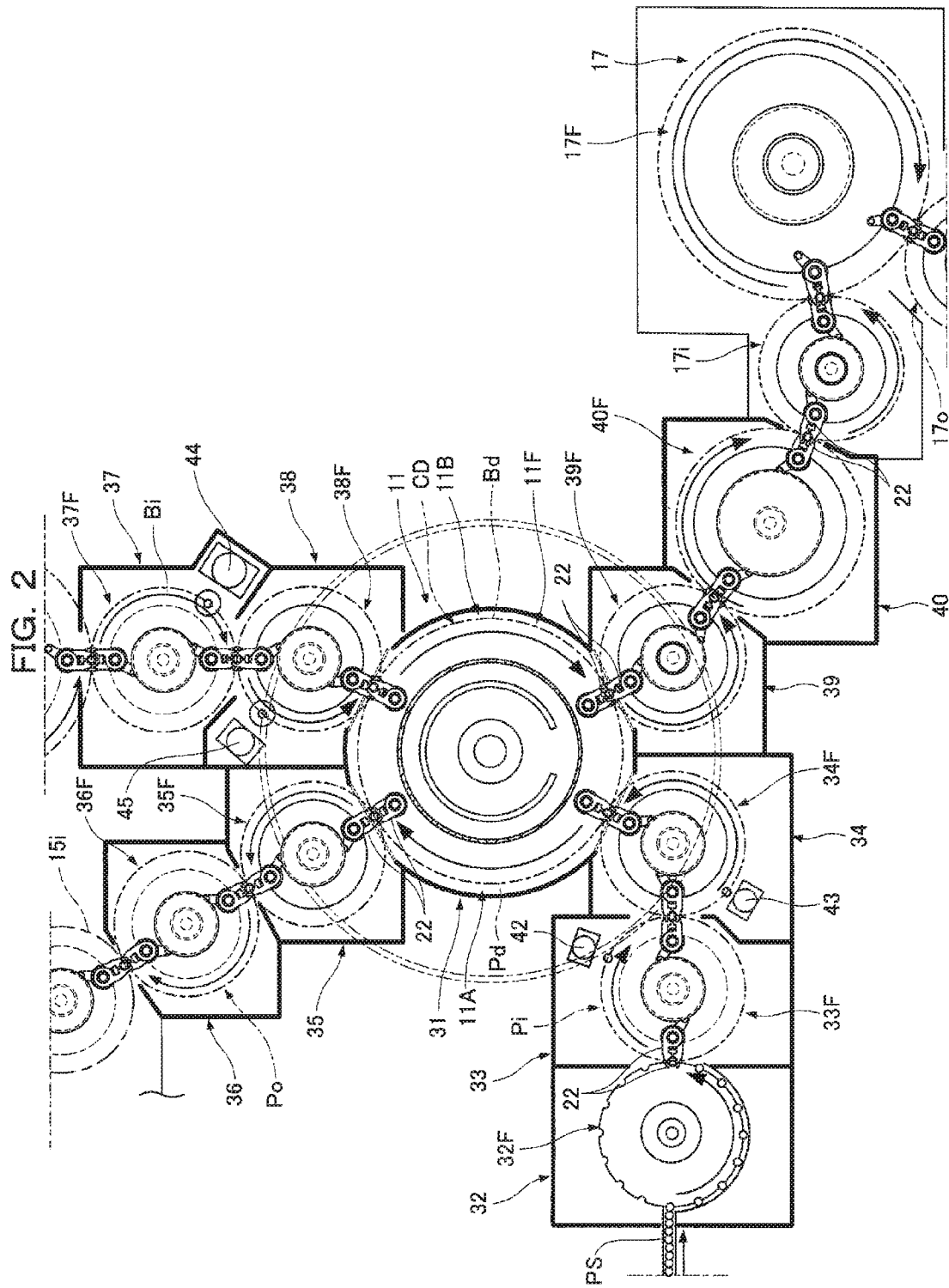
FIG. 2 is a plan view showing an electron beam sterilization device for the sterile filling equipment.
Figure 5:
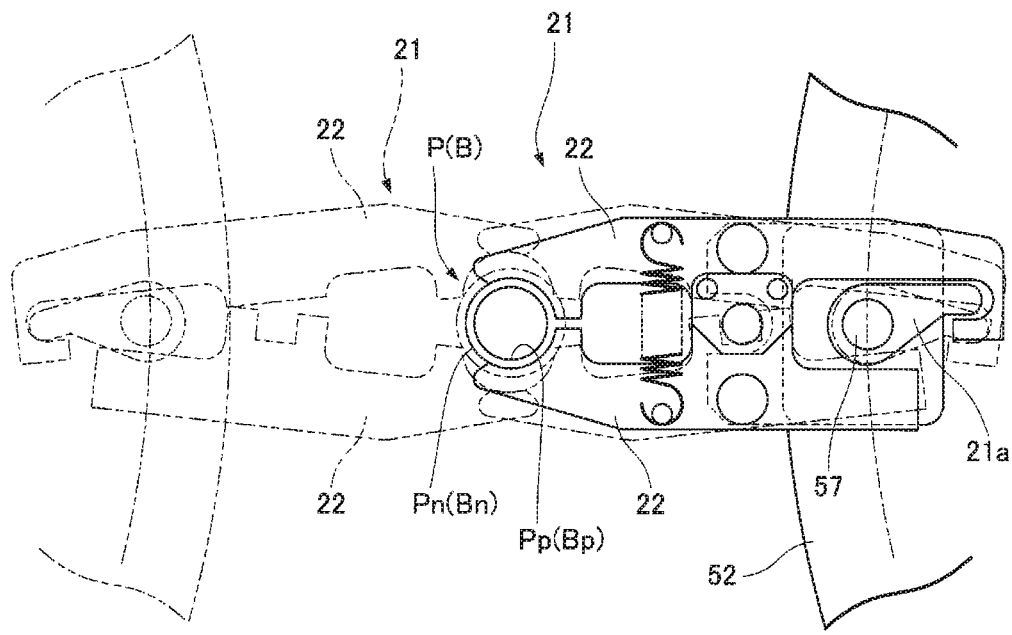
FIG. 5 is a plan view showing clamp arms.

As shown in FIGS. 1 and 2, the electron beam sterilization device 11, the filling device 12, the blow molding device 16 (will be specifically described later), the air rinser 17, and the capper 18 respectively include a rotary sterilization carrier device 11F, a rotary filling carrier device 12F, a molding carrier device 16F, a rotary cleaning carrier device 17F, and the rotary capping carrier device 18F that transport the preforms P or the molded containers B along the circular conveyance paths Pd, Bd, BF, BM, BC, and BS. As shown in FIG. 5, the rotary carrier devices 11F, 12F, 16F, 17F, and 18F each include container holders 21 disposed at regular intervals on the outer periphery of a turning table, the container holder 21 having a pair of clamp arms 22 capable of holding the neck portions of the preform P and the molded container B. The container holder 21 is provided with an attached mechanism for performing additional operations such as the raising and lowering of the containers depending on the purpose of use. Reference numeral 21a denotes an open/close cam that is open and closed by an open/close shaft 21b.

The neck handling wheels 12i, 12o, 15i, 15o, 16i, 16o, 17i, and 17o configured simply for transportation include the container holders 21 shown in FIG. 5. The container holders 21 are disposed at regular intervals on the outer periphery of a turning plate.

The blow molding device 16 includes the molding carrier device 16F having a molding air nozzle or a mold. The preforms P transported along the circular transport paths are molded into the molded containers B.

The preheating device 15 includes a preheating carrier device 15F that is a chain carrier provided with a chain (belt-like member) looped over a pair of wheels. The neck portion Pn and the opening portion Pp of the preform P are held by a holder provided on the chain. The preforms P are sequentially transported along the oblong endless preheating path PH and the body portions Pb of the preforms P are preheated to the drawing temperature by a preheater (not shown).

The preform P is transported to the blow molding device 16 from the exit neck handling wheel 15o of the preheating device 15 through the intermediate neck handling wheel 15m and the entrance neck handling wheel 16i.

Electron Beam Sterilization Device

Front Sterilization Path

Figure 3:
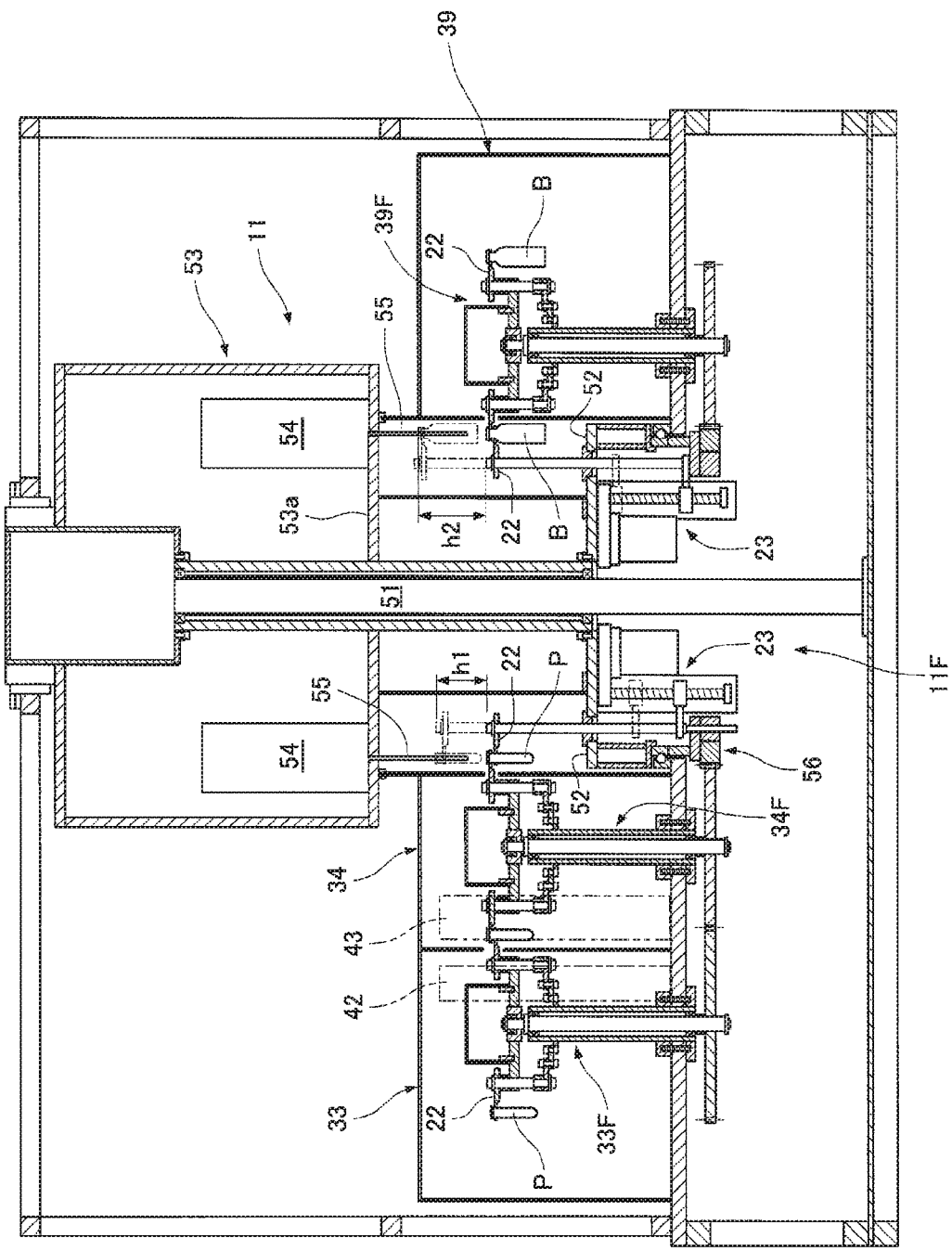
FIG. 3 is a longitudinal section of the electron beam sterilization device.

As shown in FIGS. 2 and 3, the electron beam sterilization device 11 includes a plurality of shield chambers 31 to 36 that can block electron beams. The shield chambers 31 to 36 include the main shield chamber 31 having the sterilization path CD, and the first, second, and third shield chambers 32, 33, and 34 provided along the preform entrance path Pi with the entrances and exits connected to each other. The first to third shield chambers 32 to 34 include first, second, and third intermediate carrier devices 32F, 33F, and 34F of star-wheel type connected in series. The fourth and fifth shield chambers 35 and 36 that prevent leakage of electron beams and X-rays are disposed with the entrance and exit connected to each other on the preform exit path Po. Moreover, the fourth and fifth shield chambers 35 and 36 include fourth and fifth intermediate carrier devices 35F and 36F connected in series.

A first external irradiation device 42 that sterilizes one half side of the preform P with electron beams is provided near the exit of the second shield chamber 33. A second external irradiation device 43 that sterilizes the other half side of the preform P with electron beams is provided near the entrance of the second shield chamber 34. The first and second external irradiation devices 42 and 43 are set close to each other at the entrance and the exit so as to prevent bacteria from moving from the other half side to the sterilized half side and contaminating the sterilized half side after sterilizing the one half side of the preform P.

Rear Sterilization Path

The molded container entrance path Bi connecting the molding path BM of the blow molding device 16 and the rear sterilization path Bd has a sixth shield chamber 37 and a seventh shield chamber 38 that are disposed with the entrance and exit connected to each other. The sixth and seventh shield chambers 37 and 38 contain sixth and seventh intermediate carrier devices 37F and 38F connected in series. Moreover, eighth and ninth shield chambers 39 and 40 that prevent leakage of electron beams and X-rays are disposed with the entrance and exit connected to each other on the molded container exit path Bo. Furthermore, the eighth and ninth shield chambers 39 and 40 contain eighth and ninth intermediate carrier devices 39F and 40F connected in series.

The sixth shield chamber 37 contains a third external irradiation device 44 that sterilizes one half side of the molded container B with electron beams. A fourth external irradiation device 45 that sterilizes the other half side of the molded container B with electron beams is provided near the entrance of the seventh shield chamber 38. The third and fourth external irradiation devices 44 and 45 are set close to each other at the entrance and the exit so as to prevent bacteria from moving from the other half side to the sterilized half side and contaminating the sterilized half side after sterilizing the one half side of the molded container B.

Main Shield Chamber

Figure 4:
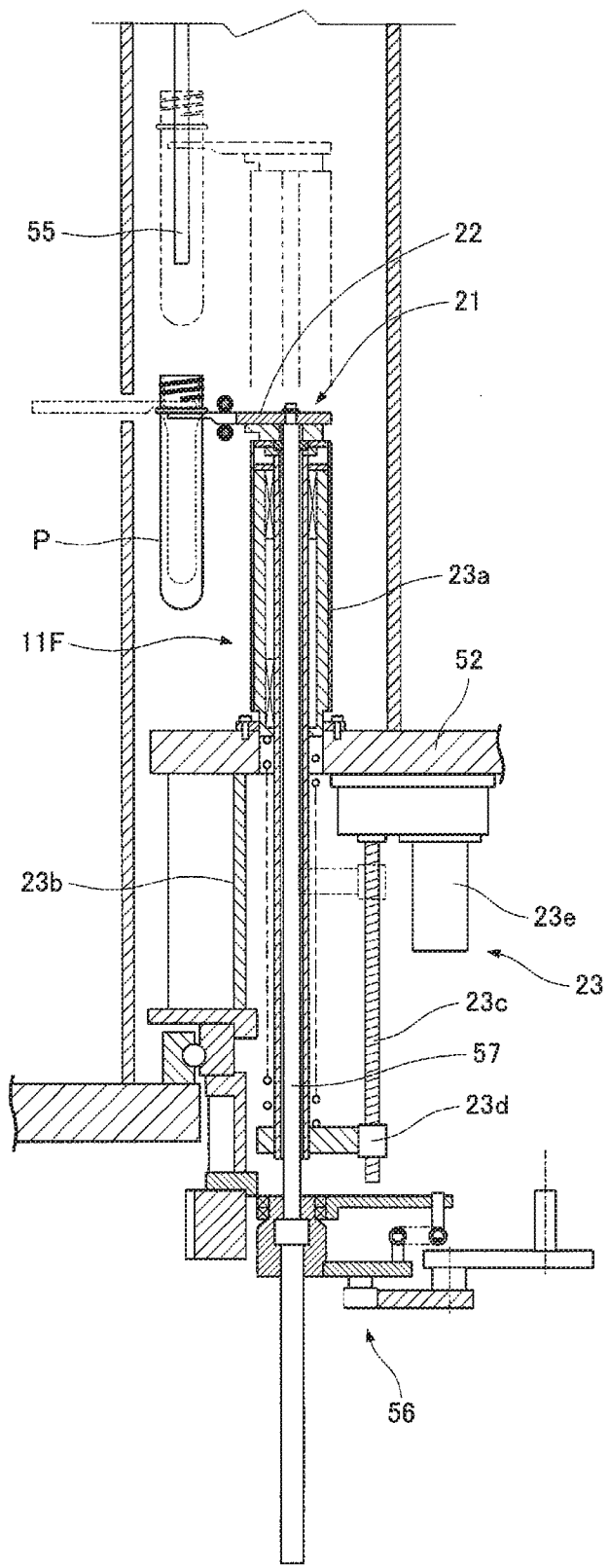
FIG. 4 is a longitudinal section showing a container holder for the electron beam sterilization device.

As shown in FIG. 3, the sterilization carrier device 11F that transports the preform P and the molded container B along the sterilization path CD in the main shield chamber 31 has a turning table 52 rotatably supported by a main shaft 51 for rotations. The turning table 52 is rotated at a predetermined speed by a turning device (not shown). The container holders 21 having the clamp arms 22 are disposed at regular intervals on the outer periphery of the turning table 52 via a container elevating device (nozzle inserting device) 23. As shown in FIG. 4, the clamp arms 22 are provided on the upper end of the container elevating device 23. The container elevating device 23 includes an elevating shaft cylinder 23b that is supported by a guide member 23a so as to move up and down, a screw shaft 23c disposed in parallel with the elevating shaft cylinder 23b, an internal thread member 23d that is connected to the lower part of the elevating shaft cylinder 32b and is screwed onto the screw shaft 23c, and a servo motor 23e that rotates the screw shaft 23c through a speed reducer. As shown in FIG. 3, the preform P held by the clamp arms 22 is lifted by a predetermined distance h1 on the front sterilization path Pd while the molded container B held by the clamp arms 22 is lifted by a predetermined distance h2 on the rear sterilization path Bd.

An outer shield 53 that rotates about the main shaft 51 in synchronization with the turning table 52 is disposed in the upper part of the main shield chamber 31. Internal irradiation devices 54 corresponding to the container holders 21 are provided on a bottom wall 53a. The internal irradiation device 54 has an electron beam irradiation nozzle 55 for internal sterilization. The electron beam irradiation nozzle 55 is hung into the main shield chamber 31 penetrated through the bottom wall 53a. Reference numeral 56 denotes a cam arm open/close device that opens and closes the clamp arms 22 through a central axis 57.

Sterilizing Operation

In this configuration, the preforms P are transported from the preform feeder 13 along the preform supply path PS, are arranged by the cleaning/positioning device 14, and then are sequentially supplied to the electron beam sterilization device 11. In the electron beam sterilization device 11, the first to third intermediate carrier devices 32F to 34F transport the preforms P from the first to third shield chambers 32 to 34 to the main shield chamber 31 along the preform entrance path Pi. During the transportation, the preforms P are irradiated with electron beams from the first external irradiation device 42 in the second shield chamber 33 and then are irradiated with electron beams from the second external irradiation device 43 in the third shield chamber 34. This sterilizes the overall outer surfaces of the preforms P and transports the preforms P to the sterilization carrier device 11F.

On the front sterilization path Pd of the preform sterilization section 11A, the preform P held by the container holder 21 via the clamp arms 22 is lifted only by the predetermined distance h1 by the container elevating device 23, and then the electron beam irradiation nozzle 45 is inserted into the body portion Pb from the opening portion Pp so as to sterilize the inner surface of the preform P.

In this way, the internally and externally sterilized preform P is transported to the preheating device 15, is heated to the molding temperature, and then is transported to the blow molding device 16. In the blow molding device 16, the preform P is molded into the molded container B and then the molded container B is transported to the electron beam sterilization device 11.

In the electron beam sterilization device 11, the sixth and seventh intermediate carrier devices 37F and 38F transport the molded containers B from the sixth and seventh shield chambers 37 and 38 to the main shield chamber 31 along the molded container entrance path Bi. In the sixth shield chamber 37, the molded container B is irradiated with electron beams from the third external irradiation device 44. In the seventh shield chamber 38, the molded container B is irradiated with electron beams from the fourth external irradiation device 45. This sterilizes the overall outer surfaces of the molded containers B and transports the molded containers B to the sterilization carrier device 11F.

On the rear sterilization path Bd of the molded-container sterilization section 11B, the molded container B held by the container holder 21 via the clamp arms 22 is lifted only by the predetermined distance h2 (h2>h1) by the container elevating device 23, and then the electron beam irradiation nozzle 45 is inserted into the body portion Pb from the opening portion Bp of the molded container B so as to sterilize the inner surface of the molded container B with electron beams emitted from an emission port on the lower end of the nozzle.

The externally and internally sterilized molded container B is transported from the rear sterilization path Bd to the eighth and ninth shield chambers 39 and 40 by the eighth and ninth intermediate carrier devices 39F and 40F and then is transported to the air rinser 17 through the entrance neck handling wheel 17i. In the air rinser 17, when the molded container B is transported on the cleaning path BC by the cleaning carrier device 17F having a reversal mechanism, clean air (inert gas (nitrogen gas) or wash water may be used depending on the kind of filling liquid) is blown into the reversed molded container B so as to replace ozone with the clean air while washing off residues (hardly remain) in the molded container B. The air rinser 17 may be replaced with an internal gas replacing device that replaces ozone in the molded container B with clean air or inert gas (nitrogen gas). Since ozone generated in the electron beam sterilization device 11 is brought with the molded containers B into the air rinser 17, the air rinser 17 has a gas cleaner for discharging ozone.

Subsequently, the molded container B is transported to the filling device 12 from the air rinser 17 through the exit neck handling wheel 17o, the intermediate neck handling wheel 17m, and the entrance neck handling wheel 12i and then is filled with filling liquid during transportation along the filling path BF. The molded container B is then transported to the capper 18 through the exit neck handling wheel 12o and a clean cap transported from the cap cleaning device 19C is attached to the opening portion Bp of the molded container B so as to seal the molded container B.

Effect of First Embodiment

According to the electron beam sterilization device 11, the endless sterilization path CD is divided into the front sterilization path Pd and the rear sterilization path Bd, the preform sterilization section 11A for sterilizing the preform P is provided on the front sterilization path Pd, and the molded-container sterilization section 11B for sterilizing the molded container B is provided on the rear sterilization path Bd. The preform P and the molded container B can be thus simultaneously sterilized by the single electron beam sterilization device 11, achieving more stable sterilization. Moreover, the preform P having a small surface area can be sterilized with a small electron dose, thereby reducing the size of the preform sterilization section 11A. The molded container B formed by blow molding on the preform P previously sterilized on the front sterilization path Pd is hardly contaminated, thereby considerably reducing an electron dose in the molded-container sterilization section 11B. This can shorten the front sterilization path Pd and the rear sterilization path Pd and reduce the size of the internal irradiation device for generating electron beams and the size of the electron beam sterilization device 11.

The preforms P and the molded containers B are internally sterilized in a sequential manner after external sterilization. Thus, contaminants deposited on the unsterilized inner surfaces of the preforms P and the molded containers B are hardly deposited from the opening portions onto the sterilized outer surfaces of the preforms P and the molded containers B. This can effectively prevent contamination from an unsterilized portion to a sterilized portion.

Furthermore, the neck portions Pn and Bn of the preform P and the molded container B are identical in shape and thus the clamp arms 22 for holding the preform P or the molded container B can be identical in shape and hold the neck portions Pn and Bn according to the same operation on the sterilization path. This can simplify the sterilization device with a small size.

Moreover, the molded container B is formed by blow molding on the preform P having undergone preliminary sterilization. This can reduce the irradiation time and intensity of electron beams in external and internal sterilization, achieving effective sterilization. Since the preform P and the molded container B can be sterilized by the single electron beam sterilization device 11, the size of the equipment can be reduced.

Moreover, the preform P having a small surface area can be sterilized with a small electron dose, thereby considerably reducing the electron doses of the first and second external irradiation devices 42 and 43 and the internal irradiation device 54 used in the preform sterilization section 11A. This can reduce the size of the equipment. Furthermore, the molded container B formed by blow molding on the externally and internally sterilized preform P is hardly contaminated, thereby considerably reducing the electron doses of the third and fourth external irradiation devices 44 and 45 and the internal irradiation device 54 used in the molded-container sterilization section 11B. This can shorten the front sterilization path Pd and the rear sterilization path Bd and reduce the size of the internal irradiation device for generating electron beams and the size of the electron beam sterilization device 11, contributing to a size reduction of the overall equipment.

Modification of the Electron Beam Sterilization Device

In the first embodiment, the electron beam irradiation nozzles 55 are fixed and the container elevating devices (nozzle inserting devices) 23 raise or lower the preforms P and the molded containers B so as to insert the electron beam irradiation nozzles 55 into the preforms P and the molded containers B. In a first modification in FIG. 7A, the nozzle inserting devices raise or lower the electron beam irradiation nozzles 55 and the container holders 21 for holding the preforms P or the molded containers B are fixed to the nozzle inserting devices. Substantially the same members as those of the first embodiment are indicated by the same reference numerals and the explanation thereof is omitted.

Figure 7A:
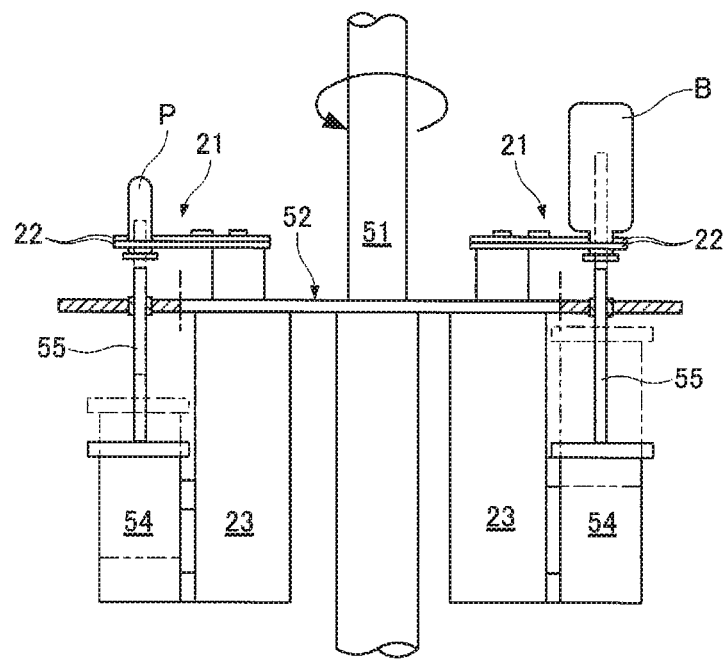
FIGS. 7A and 7B show another embodiment of the electron beam sterilization device.

Specifically, as shown in FIG. 7A, the internal irradiation device 54 is disposed at the bottom of the turning table 52, which rotates about the main shaft 51, via the elevating device 23. The electron beam irradiation nozzle 55 raised on the internal irradiation device 54 protrudes and retracts upward from and into a through hole on the turning table 52. The container holder 21 is fixed and disposed on the upper side of the turning table 52.

With this configuration, the heavy internal irradiation device 54 and the power supply thereof can be disposed at the bottom of the turning table 52. This can stably rotate the turning table 52 so as to achieve high-speed sterilization and filling.

Figure 7B:
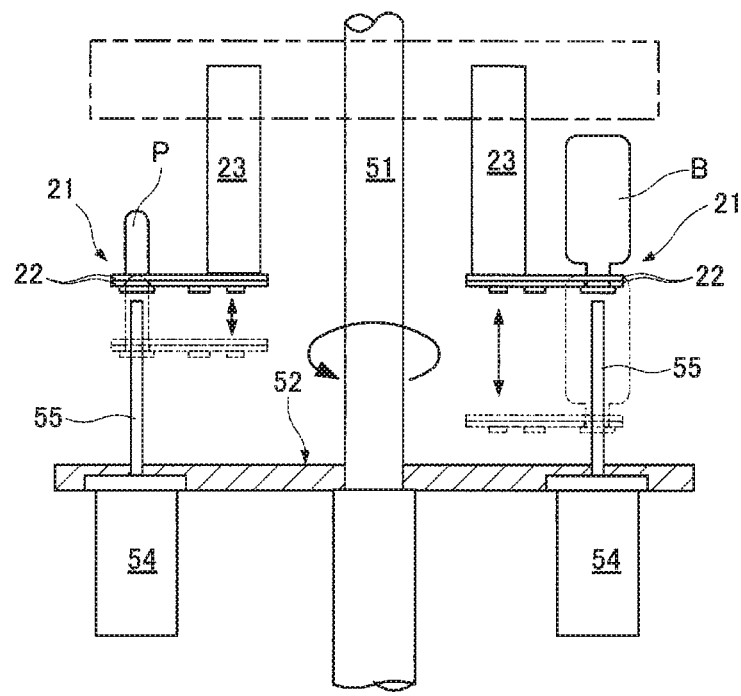

FIG. 7B shows a second modification in which the electron beam irradiation nozzles 55 of the first embodiment and the container holders 21 for holding the preforms P or the molded containers B are vertically inverted. Specifically, the internal irradiation devices 54 are disposed on the outer periphery of the turning table 52 so as to raise the electron beam irradiation nozzles 55 at predetermined intervals, and the container holders 21 for holding the inverted preforms P or molded containers B are opposed to the tops of the electron beam irradiation nozzles 55 via the container elevating devices (nozzle inserting devices) 23. This configuration can obtain the same effect as those of the first embodiment and the first modification.

Having described the invention, the following is claimed:
1. An electron beam sterilization device capable of simultaneously sterilizing a molded container and a preform of the molded container, the electron beam sterilization device comprising:
electron beam irradiation nozzles that are protruded at regular intervals and are moved along an endless sterilization path;
container holders that are moved along the sterilization path so to hold the molded container and the preform; and
a nozzle inserting/removing device that moves one of the container holder and the electron beam irradiation nozzle to the other so as to insert and remove the electron beam irradiation nozzle into and from the molded container and the preform,
wherein the sterilization path partially serves as a front sterilization path where a container carrier device holds and transports the preform while the other part of the transport path serves as a rear sterilization path where the container carrier device holds and transports the molded container,
the front sterilization path has a preform sterilization section where the nozzle inserting/removing device inserts a distal end of the electron beam irradiation nozzle into the preform from an opening portion and internally sterilizes the preform while the rear sterilization path has a molded-container sterilization section where the nozzle inserting/removing device inserts the distal end of the electron beam irradiation nozzle into the molded container from the opening portion and internally sterilizes the molded container.

2. The electron beam sterilization device according to claim 1, further comprising a front external electron-beam emitter on a preform entrance path connected to an entrance of the front sterilization path, the front external electron-beam emitter sterilizing an outer surface of the preform with electron beams; and
a rear external electron-beam emitter on a molded-container entrance path connected to an entrance of the rear sterilization path, the rear external electron-beam emitter sterilizing an outer surface of the molded container.

3. The electron beam sterilization device according to one of claims 1 and 2, wherein the preform and the molded container have neck portions that are substantially identical in shape, and
the container holder comprises a pair of clamp arms capable of holding the neck portions of the preform and the molded container.

4. Sterile filling equipment comprising a blow molding device that forms a molded container by performing blow molding on a preform of the molded container, and a filling device that fills, with a content fluid, the molded container formed by the blow molding device,
the sterile filling equipment further comprising the electron beam sterilization device according to one of claims 1 and 2, the electron beam sterilization device sterilizing the preform before transportation into the blow molding device and the molded container ejected from the blow molding device.

5. The sterile filling equipment according to claim 4, further comprising a preform preheating device on a transport path from the preform sterilization section to the blow molding device; and
a molded-container cleaning device on a transport path from the molded-container sterilization section to the filling device.

* * * * *